(12) United States Patent
Chan et al.

(10) Patent No.: US 9,144,661 B2
(45) Date of Patent: Sep. 29, 2015

(54) REINFORCED ELONGATE MEDICAL DEVICE AND METHOD OF MANUFACTURE

(71) Applicants: Stryker Corporation, Kalamazoo, IN (US); Stryker NV Operations Limited, Dublin (IE)

(72) Inventors: Huey Chan, San Jose, CA (US); Sean McFerran, Newark, CA (US)

(73) Assignees: STRYKER CORPORATION, Kalamazoo, MI (US); STRYKER EUROPEAN HOLDINGS I, LLC, Kalamazoo, MI (US)

( * ) Notice: Subject to any disclaimer, the term of this patent is extended or adjusted under 35 U.S.C. 154(b) by 333 days.

(21) Appl. No.: 13/686,695

(22) Filed: Nov. 27, 2012

(65) Prior Publication Data

US 2013/0144267 A1    Jun. 6, 2013

Related U.S. Application Data

(60) Provisional application No. 61/567,059, filed on Dec. 5, 2011.

(51) Int. Cl.
| | | |
|---|---|---|
| *A61M 25/00* | (2006.01) | |
| *A61B 1/005* | (2006.01) | |
| *A61B 17/11* | (2006.01) | |
| *A61B 17/00* | (2006.01) | |
| *A61B 17/12* | (2006.01) | |

(52) U.S. Cl.
CPC ............ *A61M 25/0054* (2013.01); *A61B 1/005* (2013.01); *A61M 25/0009* (2013.01); *A61M 25/0053* (2013.01); *A61B 17/11* (2013.01); *A61B 2017/00309* (2013.01); *A61B 2017/1205* (2013.01); *A61M 25/0013* (2013.01); *Y10T 156/1002* (2015.01)

(58) Field of Classification Search
CPC ................ A61B 2017/00309; A61M 25/0009; A61M 25/0013; A61M 25/0053; A61M 25/0054
USPC .................................................. 604/524, 525
See application file for complete search history.

(56) References Cited

U.S. PATENT DOCUMENTS

2007/0100285 A1* 5/2007 Griffin et al. ............ 604/164.11

FOREIGN PATENT DOCUMENTS

| EP | 1 042 997 A1 | 11/2000 |
|---|---|---|
| WO | 01/00112 A1 | 1/2001 |

OTHER PUBLICATIONS

PCT Invitation to Pay Additional Fees for International Application No. PCT/US2012/066672, Applicant Stryker Corporation, Form PCT/ISA/206 and Annex to Form PCT/ISA/206, dated Feb. 25, 2013 (6 pages).
PCT International Search Report and Written Opinion for International Application No. PCT/US2012/066672, Applicant Stryker Corporation, Forms PCT/ISA/220, PCT/ISA/237 and PCT/ISA/210, mailed Apr. 10, 2013 (14 pages).

* cited by examiner

*Primary Examiner* — Kevin C Sirmons
*Assistant Examiner* — Deanna K Hall
(74) *Attorney, Agent, or Firm* — Vista IP Law Group LLP

(57) ABSTRACT

An elongate medical device includes an elongate core and a substantially flat sheet formed into a tubular body defining a longitudinal axis and disposed around at least a portion of the elongate core, where the flat sheet has a length, and where a cross-sectional thickness of the sheet varies along the length of the sheet. The tubular body has proximal and distal portions, and a cross-sectional thickness of the sheet forming the distal portion of the tubular body may be less than a cross-sectional thickness of the sheet forming the proximal portion of the tubular body. A cross-sectional thickness of the sheet forming the tubular body preferably tapers from the proximal portion to the distal portion.

25 Claims, 5 Drawing Sheets

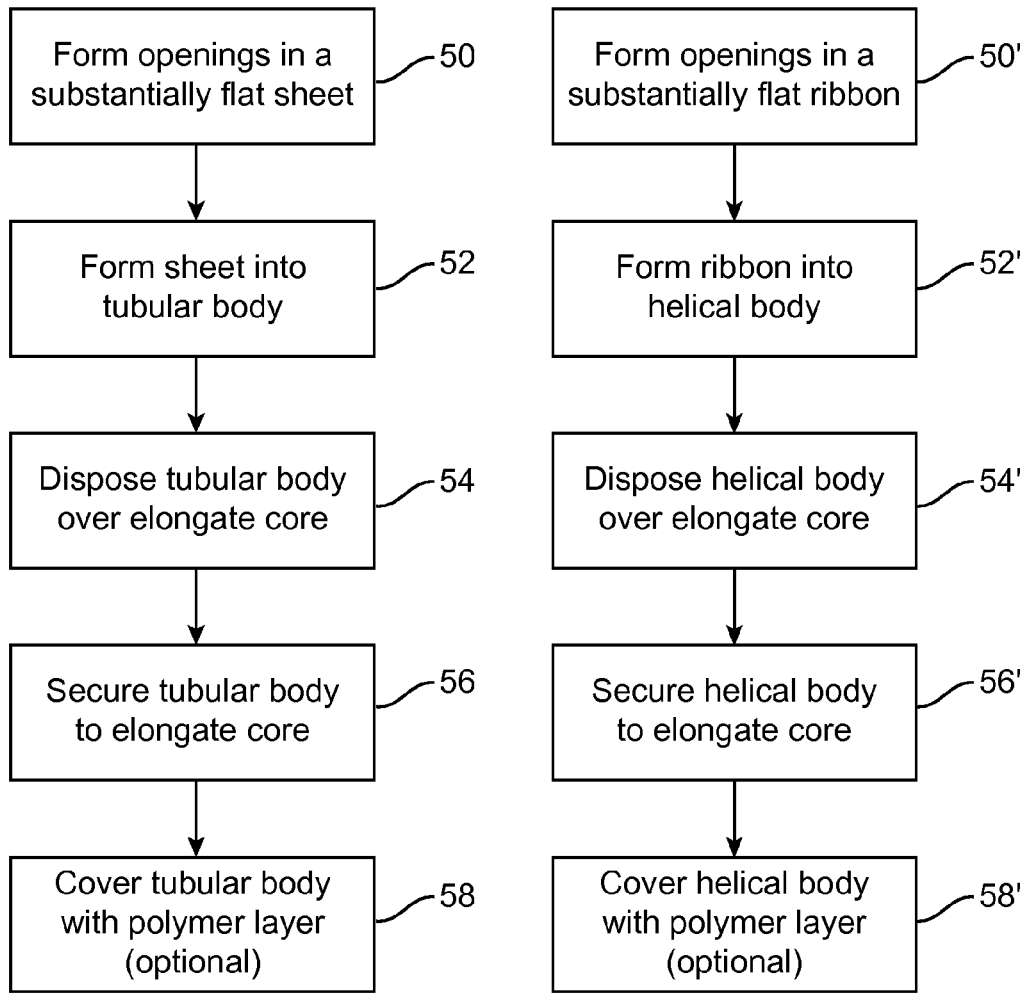

REINFORCED ELONGATE MEDICAL DEVICE AND METHOD OF MANUFACTURE

RELATED APPLICATION DATA

The present application claims the benefit under 35 U.S.C. §119 to U.S. provisional patent application Ser. No. 61/567,059, filed Dec. 5, 2011. The foregoing application is hereby incorporated by reference into the present application in its entirety.

FIELD OF THE INVENTION

The field of the invention generally relates to elongate medical devices. More particularly, the invention relates to reinforced elongate medical devices, such as reinforced intravascular catheters and guidewires.

BACKGROUND

The use of intravascular medical devices has become an effective method for treating many types of vascular disease. In general, a suitable intravascular device, such as an intravascular catheter, is inserted into the vascular system of the patient and navigated through the vasculature to a desired target site. Using this method, virtually any target site in the patient's vascular system may be accessed, including the coronary, cerebral, and peripheral vasculature.

The catheter typically enters the patient's vasculature at a convenient location, such as a blood vessel in the neck or near the groin. Once the distal portion of the catheter (i.e., the portion farthest from the proximal handle of the catheter) has entered the patient's vascular system, the distal tip may be urged toward the target site by applying an axial force to the proximal portion of the catheter. Catheters having a relatively high level of pushability and kink resistance more effectively communicate this axial force.

Catheters frequently travel through the vascular system in a tortuous path, and are often required to change direction and to even double back on itself. The catheter may be "steered" by applying torsional forces to the proximal portion of the catheter. Catheters having a relatively high level of torqueability facilitate the steering process. Further, catheters having a relatively high level of flexibility are effectively conform to a patient's tortuous vascular system.

The distance between the access site and the target site is often in excess of 100 cm. The inside diameter of the vasculature at the access site is often less than 5 mm. In view of the geometry of the patient's body, it is desirable to combine the features of torqueability, pushability, kink resistance, and flexibility into a catheter, which is relatively long and has a relatively small diameter. It is often desirable that the catheter have a relatively high level of pushability and torqueability, particularly near its proximal end. It is also sometimes desirable that a catheter be relatively flexible and steerable, particularly near its distal end. Further, it is sometimes desirable that the lumen of the catheter provide a pathway through the catheter having a low friction surface.

The blood vessels in the brain frequently have an inside diameter of less than 3 mm. Accordingly, it is desirable that intravascular catheters intended for use in these blood vessels have an outside diameter which allows the catheter to be easily accommodated by the blood vessel. The path of the vasculature inside the brain is highly tortuous, and the blood vessels are relatively fragile. Accordingly, it is desirable that distal portion of a catheter for use in the brain be adapted to follow the highly torturous path of the neurological vasculature, for instance, by having increased flexibility.

As described above, it is desirable to combine a number of performance features in an intravascular catheter. It is desirable that the catheter have a relatively high level of pushability and torqueability, particularly near its proximal end. It is also desirable that a catheter be relatively flexible, particularly near its distal end. The need for this combination of performance features has been addressed by building a catheter out of two or more discrete tubular members having different performance characteristics. For example, a relatively flexible distal section may be bonded to a relatively rigid proximal section. When a catheter is formed from two or more discrete tubular members, it is necessary to form a bond between the distal end of one tubular member and the proximal end of another tubular member.

Reinforcement for elongate medical devices, such as catheters, typically includes several wires or other elongate bodies wrapped around a core and then encapsulated. The wires may be wound in multiple layers in different regions to adjust the degree of kink resistance. This type of design can lead to large device diameters and may not provide the appropriate amount of kink resistance and pushability for the system. Further, several design iterations may be required to balance the trade-offs in the various mechanical characteristics and to optimize the design. Moreover, because the wires are not interconnected, such reinforcement has poor torque transmission.

The above-mentioned performance features are also desirable in substantially solid intravascular devices, such as guidewires.

SUMMARY

In one embodiment, an elongate medical device includes an elongate core and a substantially flat sheet formed into a tubular body defining a longitudinal axis and disposed around at least a portion of the elongate core, where the flat sheet has a length, and where a cross-sectional thickness of the sheet varies along the length of the sheet. The tubular body has proximal and distal portions, and a cross-sectional thickness of the sheet forming the distal portion of the tubular body may be less than a cross-sectional thickness of the sheet forming the proximal portion of the tubular body. Optionally, a cross-sectional thickness of the sheet forming the tubular body tapers from the proximal portion to the distal portion.

The sheet forming the tubular body may include a plurality of constant sheet thickness sections separated by respective transition sections, where the respective constant sheet thickness sections have differing cross-sectional thicknesses. Further, the respective transition sections may have a tapered cross-sectional thickness. Alternatively or additionally, the flat sheet is rolled around the longitudinal axis to form the tubular body. Moreover, portions of the flat sheet may be removed to form openings therein. The elongate core may define a lumen therein or be substantially solid.

In another embodiment, an elongate medical device includes an elongate core and a substantially flat ribbon spirally wound into a helical body defining a longitudinal axis and disposed around at least a portion of the elongate core, where the ribbon has a length, and where a cross-sectional thickness of the ribbon varies along the length of the ribbon. The helical body has a proximal portion and a distal portion, and a cross-sectional thickness of the ribbon forming the distal portion of the helical body may be thinner than a cross-sectional thickness of the ribbon forming the proximal portion of the helical body. Optionally, a cross-sectional thickness of the ribbon forming the helical body tapers from the proximal portion to the distal portion.

The ribbon forming the helical body may include a plurality of constant ribbon thickness sections separated by respective transition sections, where the respective constant ribbon thickness sections have differing thicknesses. Further, the respective transition sections may have a tapered cross-sectional thickness. Alternatively or additionally, portions of the ribbon are removed to form openings therein. Moreover, the elongate core may define a lumen therein or be substantially solid.

In yet another embodiment, a method of forming an elongate medical device includes forming a substantially flat elongate sheet into a tubular body, the sheet having a length and a cross-sectional thickness, where the cross-sectional thickness varies along the length of the sheet, and securing the tubular body to an outer surface of an elongate core. Optionally, the method also includes, prior to forming the sheet into a tubular body, removing portions from the sheet to define openings therein. The tubular body has a longitudinal axis, and forming the sheet into a tubular body may include rolling the sheet around the longitudinal axis. The rolled sheet may be treated by heat setting, tack welding, laser welding, mechanical attachment, chemical bonding, or adhering with an adhesive. Removing portions from the sheet may include etching and/or machining a pattern of openings in the sheet. Alternatively or additionally, the method also includes covering the tubular body with a polymer layer.

In still another embodiment, a method of forming an elongate medical device, include forming a substantially flat ribbon into a helical body, the ribbon having a length and a cross-sectional thickness, where the cross-sectional thickness varies along the length of the ribbon, and securing the helical body to the outer surface of an elongate core. Optionally, the method also includes, prior to forming the ribbon into a tubular body, removing portions from the ribbon to define openings therein. The helical body has a longitudinal axis, and forming the ribbon into a helical body includes spirally winding the ribbon around the longitudinal axis. The wound ribbon may be treated by heat setting, tack welding, laser welding, mechanical attachment, chemical bonding, or adhering with an adhesive. Removing portions from the ribbon may include etching and/or machining a pattern of openings in the sheet. Alternatively or additionally, the method also includes covering the helical body with a polymer layer.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. The relative scale of select elements may have been exaggerated for clarity. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

FIGS. 9 and 10 are flow charts of methods for manufacturing elongate medical devices in accordance with various embodiments of the disclosed inventions.

DETAILED DESCRIPTION OF THE ILLUSTRATED EMBODIMENTS

Figure 1:
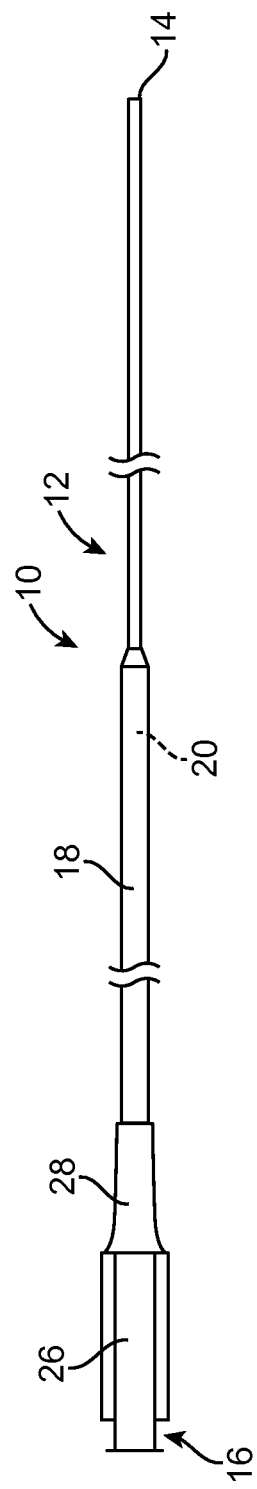
FIG. 1 is a plan view of an elongate medical device in accordance with one embodiment of the disclosed inventions.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

FIG. 1 is a plan view of an elongate medical device 10, e.g., a catheter, in accordance with one embodiment of the disclosed inventions. Device 10 includes an elongate shaft 12 having a distal end 14, a proximal end 16, an outer surface 18, and a lumen 20 extending therethrough. Device 10 further includes a hub 26 and a strain relief 28 disposed at the proximal end 16 of elongate shaft 12. Hub 26 and strain relief 28 enable a physician to connect other devices to catheter 10.

Hub 26 and strain relief 28 also provide a convenient place for to apply axial or rotational forces in order to manipulate catheter 10.

While the elongate medical device 10 is depicted as an intravascular catheter 10, and in particular, an intravascular delivery, guide and/or diagnostic catheter 10, this is for the purposes of illustration only. Other medical devices embodying aspects of the invention may relate to virtually any medical device including an elongate shaft. For example, other embodiments may relate to medical devices such as a balloon catheter, an atherectomy catheter, a drug delivery catheter, a stent delivery catheter, an endoscope, an introducer sheath, a fluid delivery device, other infusion or aspiration devices, device delivery (i.e., implantation) devices, guidewires and the like. Thus, while the figures and descriptions below are directed toward a delivery, guide, and/or diagnostic catheter, in other applications the structure and/or sizes in terms of diameter and length may vary widely, depending upon the desired properties of a particular device.

The shaft 12 may have a length and an outside diameter appropriate for its desired use, for example, to enable intravascular insertion and navigation. For example, in some embodiments, the shaft 12 may have a length in the range of about 1 cm to about 300 cm or more, or in some embodiments in the range of about 20 cm to about 250 cm, and an outside diameter in the range of about 1 F to about 20 F, or in some embodiments, in the range of about 1 F to about 10 F. Additionally, although depicted as including a generally round outer diameter and a round cross-sectional shape, it can be appreciated that the shaft 12 can include other outer diameter and/or cross-sectional shapes or combinations of shapes without departing from the spirit of the invention. For example, the outer diameter and/or cross-sectional shape of the generally tubular shaft 12 may be oval, rectangular, square, triangular, polygonal, and the like, or combinations thereof, or any other suitable shape, depending upon the desired characteristics.

In some embodiments, the catheter 10 can be a microcatheter including a shaft 12 that is adapted and/or configured for use within small anatomies of the patient. For example, some embodiments are particularly useful in treating target sites located in tortuous and/or narrow vessels. Some examples of such vessels may include those in the neurovascular system, or in certain sites within the coronary vascular system, or in sites within the peripheral vascular system such as superficial femoral, popliteal, or renal arteries. The target site in some embodiments is a neurovascular site, such as a site in the brain, which is accessible only via a tortuous vascular path. For example, a vascular path to the brain may contain a plurality of bends or turns which may be greater than about 90° turns, and/or involving vessels with diameters in the range of about 8 mm or less, and in some cases as small as about 2 to about 3 mm or less. As such, in some embodiments, the shaft 12 can include an outside diameter in the range of approximately 1 F-4 F.

However, in other embodiments, the catheter 10 may be used in other target sites within the anatomy of a patient, in which case the shaft 12 would be so adapted. For example, the catheter 10 may be suited for other uses in the digestive system, soft tissues, or any other use including insertion into an organism for medical uses, and the shaft 12 could be appropriately adapted for such uses. For example, in some embodiments, the catheter 10 may be used as an introducer sheath, in which case the shaft 12 may be significantly shorter. The catheter 10 may also include additional structure and materials adapted for a particular use and/or procedure. For example, in some other embodiments, the shaft 12 may include additional devices or structures such as inflation or anchoring members, device deployment members, sensors, optical elements, ablation devices, or the like, or any of a broad variety of other structures, depending upon the desired function and characteristics of the catheter 10.

Figure 2:
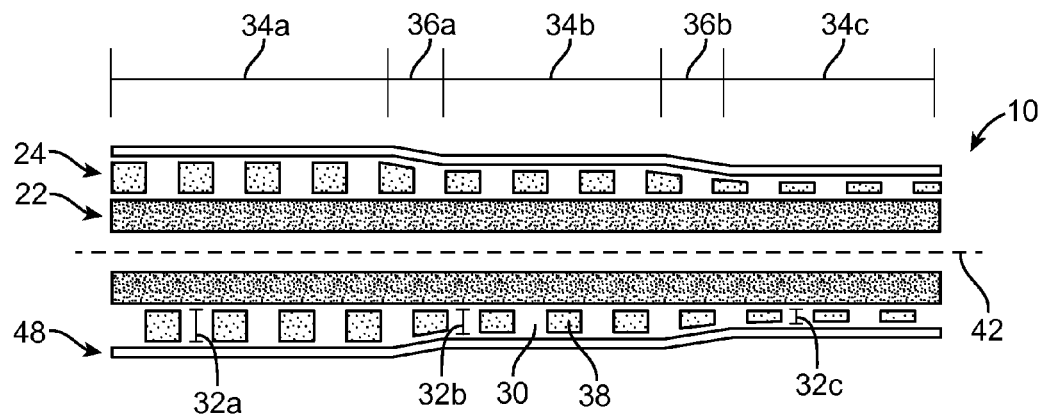
FIG. 2 is a detailed longitudinal cross-sectional view through the midline of an elongate medical device in accordance with another embodiment of the disclosed inventions.

FIG. 2 is a longitudinal cross-sectional view of an elongate medical device 10 in accordance with another embodiment of the disclosed inventions. Device 10 includes an elongate core 22 surrounded by a tubular body 24. The wall 38 of the tubular body 24 has openings 30 therein and a cross-sectional thickness 32. The cross-sectional thickness 32 varies along the length of the tubular body 24.

The elongate core 22 may have an inner diameter, for example, defining a lumen, that is in the range of about 0.01 to about 0.05 inch in size, or in the range of about 0.015 to about 0.03 inch in size, or in the range of about 0.016 to about 0.026 inch in size. As indicated above, however, the lumen (defined by the inner diameter of the elongate core 22) can be adapted and/or configured (e.g., sized) to accept other material, fluids, or medical devices, therein, and as such, the size of the lumen can vary, depending upon the desired characteristics and intended use.

Additionally, the elongate core 22 can have an outer diameter that is in the range of about 0.011 inch to about 0.055 inch in size, or in the range of about 0.015 inch to about 0.03 inch in size, or in the range of about 0.019 inch to about 0.029 inch in size. It should be understood, however, that these dimensions are provided by way of example embodiments only and that in other embodiments, the size of the inner and outer diameter of the elongate core 22 can vary greatly from the dimensions given, depending upon the desired characteristics and function of the device.

The elongate core 22, or other portions of the shaft 12, may define one or more additional lumens depending upon the desired characteristics and function of the catheter 10, and such additional lumens can be shaped, sized, adapted and/or configured the same as or different from the other lumen in the elongate core, depending upon the desired characteristic and functions.

The elongate core 22 may include and/or be made of any of a broad variety of materials and/or structures. The elongate core 22 may have a single-layer tubular construction or a multi-layer tubular construction, or a combination thereof. For example, the elongate core 22 may be a single tubular member formed by a single layer of material, or in other embodiments, may be formed by a plurality of tubular members and/or a plurality of layers of material that may be the same and/or different, but in combination form the elongate core 22. In yet other embodiments, some portions of the elongate core 22 can include a single layer construction, while other portions may include a multi-layer construction. Some examples of suitable materials can include, but are not limited to, polymers, metals, metal alloys, or composites or combinations thereof.

In other embodiments, the elongate medical device 10 is a substantially solid device, such as a guidewire. In such embodiments, the elongate core 24 is substantially solid and does not have a lumen. Accordingly, the term elongate core 24, as used herein, encompasses both elongate members having a lumen, such as those in catheters, and substantially solid elongate members, such as those in guidewires.

Some examples of some suitable polymers can include, but are not limited to, polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysulfone, nylon, perfluoro(propyl vinyl ether) (PFA), polyether-ester, some adhesive resin, such as modified polyolefin resin, polymer/metal composites, etc., or mixtures, blends or combinations thereof, and may also include or be made up of a lubricous polymer. Other suitable polymeric materials for the elongate core 22 include, but are not limited to: poly(L-lactide) (PLLA), poly(D,L-lactide) (PLA), polyglycolide (PGA), poly(L-lactide-co-D,L-lactide) (PLLA/PLA), poly (L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxybutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly (phoshate ester), poly(amino acid), poly(hydroxy butyrate), polyacrylate, polyacrylamid, poly(hydroxyethyl methacrylate), polyurethane, polysiloxane and their copolymers, or mixtures or combinations thereof. One example of a suitable polyether block ester is available under the trade name ARNITEL™, and one suitable example of a polyether block amide (PEBA) is available under the trade name PEBAX™, from ATOMCHEM POLYMERS, Birdsboro, Pa. In some embodiments, adhesive resins may be used, for example, as tie layers and/or as the material of the structures. One example of a suitable adhesive resin is a modified polyolefin resin available under the trade name ADMER™, from Mitsui Chemicals America, Inc. Additionally, polymer material can in some instances be blended with a liquid crystal polymer (LCP). For example, in some embodiments, the mixture can contain up to about 5% LCP. This has been found in some embodiments to enhance torqueability.

Some examples of suitable metals and metal alloys can include stainless steel, such as 304V, 304L, and 316L stainless steel; nickel-titanium alloy such as a superelastic (i.e., pseudoelastic) or linear elastic nitinol; nickel-chromium alloy; nickel-chromium-iron alloy; cobalt alloy; tungsten or tungsten alloys; tantalum or tantalum alloys, gold or gold alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); or the like; or other suitable metals, or combinations or alloys thereof. In some embodiments, it is desirable to use metals, or metal alloys that are suitable for metal joining techniques such as welding, soldering, brazing, crimping, friction fitting, adhesive bonding, etc.

The tubular body 24 disposed around the elongate core 22 in FIG. 2 has three constant thickness sections 34a, 34b, 34c separated by two transitional sections 36a, 36b. The proximal transitional section 36a separates the proximal constant thickness section 34a from the middle constant thickness section 34b. The distal transitional section 36b separates the middle constant thickness section 34b from the distal constant thickness section 34c.

The constant thickness sections 34a, 34b, 34c each have a substantially constant thickness 32a, 32b, 32c, respectively. Each of the thicknesses 32a, 32b, 32c differs from the other two. The proximal thickness 32a is larger than the middle thickness 32b, in turn, is larger than the distal thickness 32c. The proximal transitional section 36a has a variable cross sectional thickness, which tapers from the proximal thickness 32a down to the middle thickness 32b. The distal transitional section 36b has a variable cross sectional thickness, which tapers from the middle thickness 32b down to the distal thickness 32c.

Figure 3:
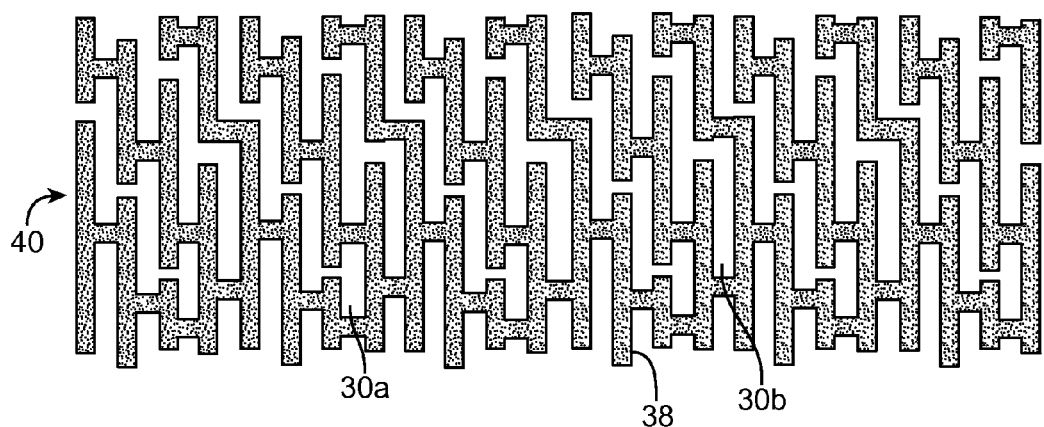
FIGS. 3 and 11 are top views of two different substantially flat sheets, each with openings formed therein.

FIG. 9 is a flow chart of a method of manufacturing the elongate medical device 10 in FIG. 2. The tubular body 24 is formed from a substantially flat sheet 40, as shown in FIG. 3. The sheet 40 has variable cross-sectional thickness 32. Examples of suitable materials for constructing the tubular body 24 include polymers, metals, or metal alloys such as those discussed above, or the like, or any of a broad variety of other suitable materials. Portions of the sheet 40 are removed to define openings 30a, 30b in the sheet 40 (step 50). Opening 30a, 30b may have different shapes, as depicted in FIG. 3, or the openings 30 may have the same shape. Examples of techniques for removing portions of the sheet 40 are chemical or laser etching, or machining, including stamping, electrical discharge machining, and grinding.

Once openings 30 are formed in the sheet 40, the sheet 40 is formed into a tubular body 24 (step 52), by first rolling the sheet 40 substantially around the longitudinal axis 42 of the tubular body 24. The rolled sheet 40 is then fixed in a tubular shape to form the tubular body 24. Methods for fixing the rolled sheet 40 include, but are not limited to, heat setting, tack welding, laser welding, mechanical attachment, chemical bonding, and adhering with an adhesive.

Figure 4:
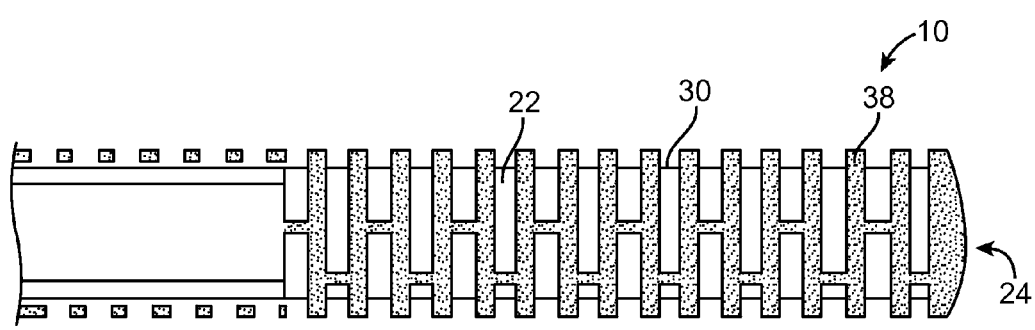
FIG. 4 is a perspective view of an elongate medical device in accordance with yet another embodiment of the disclosed inventions, with a portion of the elongate medical device shown in cross section for clarity.

The formed tubular body 24 is then disposed over the elongate core 22 (step 54), for instance, by threading the elongate core 22 through the tubular body 24. Next, the tubular body 24 is fixed to the elongate core 22 (step 56). Optionally, a coating 44 can be applied to an exterior surface of the tubular body 24 (step 58). The coating 44 may be a polymer. The reinforced elongate medical device 10 without a coating is shown in FIG. 4.

Figure 11:
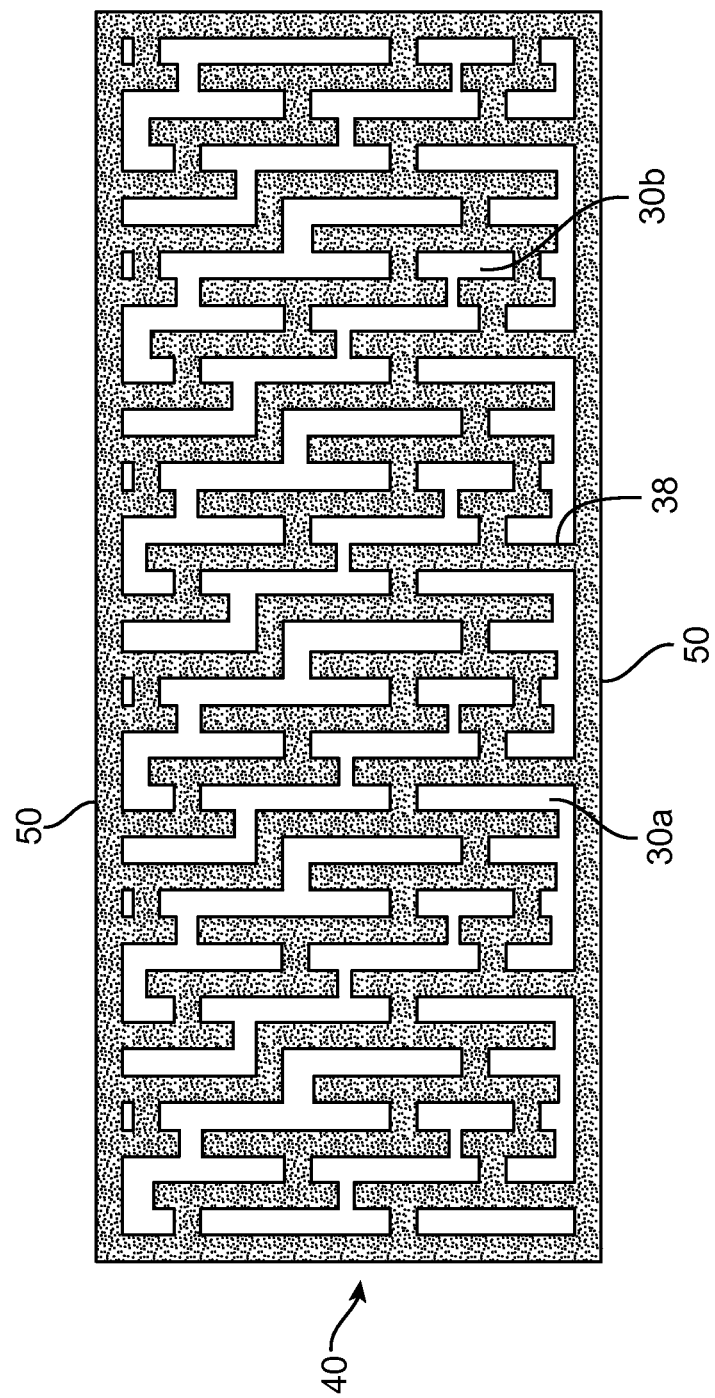

In an alternative embodiment, shown in FIG. 11, the substantially flat sheet 40 has a pair of longitudinal beams 50. In other aspects, the substantially flat sheet 40 in FIG. 11 is similar to the sheet 40 shown in FIG. 3. Due to the longitudinal beams 50, the tubular body 24 formed from the sheet 40 in FIG. 11 will be less flexible than the tubular body 24 formed form the sheet 40 in FIG. 3.

Figure 5:
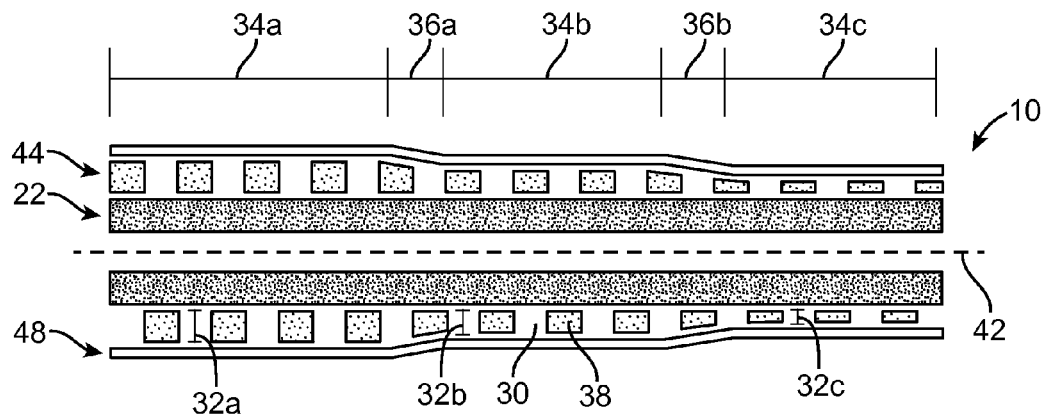
FIG. 5 is a detailed longitudinal cross-sectional view through the midline of an elongate medical device in accordance with still another embodiment of the disclosed inventions.

FIG. 5 is a longitudinal cross-sectional view of an elongate medical device 10 in accordance with yet another embodiment of the disclosed inventions. Device 10 includes an elongate core 22 surrounded by a helical body 44. The wall 38 of the helical body 44 has openings 30 therein and a cross-sectional thickness 32. The cross-sectional thickness 32 varies along the length of the helical body 44.

The helical body 44 in FIG. 5 has three constant thickness sections 34a, 34b, 34c separated by two transitional sections 36a, 36b. The proximal transitional section 36a separates the proximal constant thickness section 34a from the middle constant thickness section 34b. The distal transitional section 36b separates the middle constant thickness section 34b from the distal constant thickness section 34c.

The constant thickness sections 34a, 34b, 34c each have a substantially constant thickness 32a, 32b, 32c, respectively. Each of the thicknesses 32a, 32b, 32c differs from the other two. The proximal thickness 32a is larger than the middle thickness 32b, in turn, is larger than the distal thickness 32c. The proximal transitional section 36a has a variable cross sectional thickness, which tapers from the proximal thickness 32a down to the middle thickness 32b. The distal transitional section 36b has a variable cross sectional thickness, which tapers from the middle thickness 32b down to the distal thickness 32c.

Figure 6:
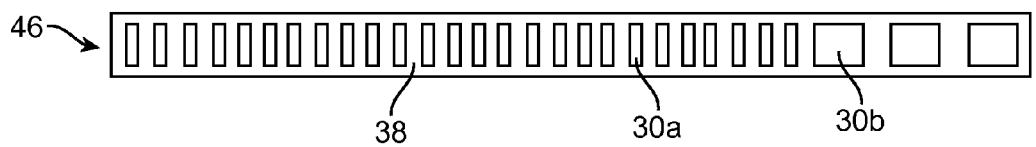
FIG. 6 is a top view of a substantially flat ribbon with openings therein.

FIG. 10 is a flow chart of a method of manufacturing the elongate medical device 10 in FIG. 5. The helical body 44 is formed from a substantially flat ribbon 46, as shown in FIG. 6. The ribbon 46 has variable cross-sectional thickness 32. Examples of suitable materials for constructing the helical body 44 include polymers, metals, or metal alloys such as those discussed above, or the like, or any of a broad variety of other suitable materials. Portions of the ribbon 46 are removed to define openings 30 in the ribbon 46 (step 50'). Examples of techniques for removing portions of the ribbon 46 are chemical or laser etching, or machining, including stamping, electrical discharge machining, and grinding.

Figure 7:
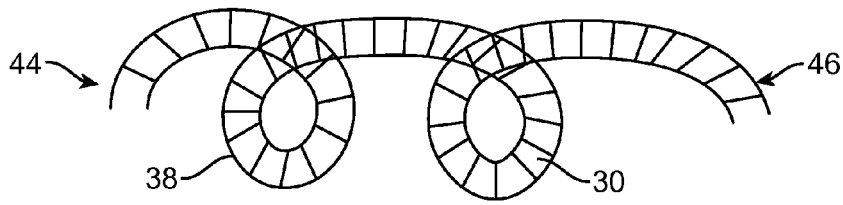
FIG. 7 is a perspective view of a helical body.

Once, openings 30 are formed in the ribbon 46, the ribbon 46 is formed into a helical body 44 (step 52'), by first helically winding the ribbon 46 substantially around the longitudinal axis 42 of the helical body 44. See, FIG. 7. The wound ribbon 46 is then fixed in a helical shape to form the helical body 44. Methods for fixing the wound ribbon 46 include, but are not limited to, heat setting, tack welding, laser welding, mechanical attachment, chemical bonding, and adhering with an adhesive.

Figure 8:
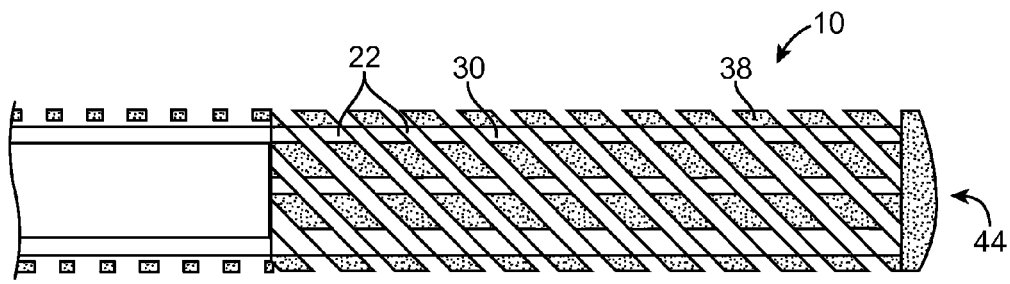
FIG. 8 is a perspective view of an elongate medical device in accordance with another embodiment of the disclosed inventions, with a portion of the elongate medical device shown in cross section for clarity.

The formed helical body 44 is then disposed over the elongate core 22 (step 54'), for instance, by threading the elongate core 22 through the helical body 44. Next, the helical body 44 is fixed to the elongate core 22 (step 56'). Optionally, a coating 44 can be applied to an exterior surface of the helical body 44 (step 58'). The coating 44 may be a polymer. The reinforced elongate medical device 10 without a coating 44 is shown in FIG. 8. Alternatively, the substantially flat ribbon 46, with the openings 30 formed therein, can be wrapped around the elongate core 22 to form the elongate medical device 10.

Forming the tubular and helical bodies 24, 44 respectively from a single sheet 40 and a single ribbon 46 improves pushability compared to multiple wound segments because there are no breaks in the single sheet 40 and the single ribbon 46. Respectively forming the tubular and helical bodies 24, 44 from a single sheet 40 and a single ribbon 46 also improves torqueability because the entire helical body 44 is interconnected, improving transmission of rotational force. The construction of the tubular and helical bodies 24, 44 also reduces the diameter of the elongate medical devices 10 because of the ability to precisely control wall 38 thicknesses by controlling the thickness of the initial substrate (sheet 40 or ribbon 46). The control of wall 38 thickness is especially important at the distal end 14 of the elongate medical device 10.

The tubular body 24 and helical body 44 in the embodiments shown in FIGS. 2 and 5 each have three cross-sectional thicknesses (32a, 32b, 32c) that decrease from one end of the elongate medical device 10 to the other. The number and pattern of cross-sectional thicknesses can be adjusted to provide the kink resistance and stiffness appropriate for the application. For instance, the cross-sectional thickness of the tubular or helical body 24, 44 may taper from one end of the elongate medical device 10 to the other with a constant slope. All numbers and patterns of cross-sectional thickness of tubular or helical bodies 24, 44 are included in the scope of the disclosed inventions.

The disclosed elongate medical devices 10 have a unique combination of mechanical properties, i.e., a flexible, torqueable, pushable, and kink resistant distal end 14 combined with a supportive, low profile proximal end 16. As such, a catheter according to the disclosed inventions is optimized for neurovascular access, but is also able to support the loads required to deliver stents or other intraluminal devices.

Such catheter typically works by accessing selected neurovascular sites with the use of a guide catheter, a guide wire, and a catheter. The guide wire is typically placed within the catheter, which is placed within the guide catheter. The guide wire and catheter system is used to track to the selected neurovascular site. Once the wire is removed from the catheter it is then positioned to treat vascular diseases such as, but not limited to, aneurysms.

While embodiments have been shown and described, various modifications may be made without departing from the scope of the inventive concepts disclosed herein. The invention(s), therefore, should not be limited, except to the following claims, and their equivalents.

What is claimed is:

1. An elongate medical device, comprising:
   an elongate core; and
   a substantially flat sheet having a length, the flat sheet formed into a tubular body defining a longitudinal axis by rolling the sheet about a longitudinal axis along the length of the sheet to form the tubular body having a length substantially the same length of the flat sheet, the tubular body permanently secured to at least a portion of the elongate core; and
   wherein a cross-sectional thickness of the sheet varies along the length of the sheet.

2. The device of claim 1, wherein the tubular body has proximal and distal portions, and wherein a cross-sectional thickness of the sheet forming the distal portion of the tubular body is less than a cross-sectional thickness of the sheet forming the proximal portion of the tubular body.

3. The device of claim 2, wherein a cross-sectional thickness of the sheet forming the tubular body tapers from the proximal portion to the distal portion.

4. The device of claim 1, wherein the sheet forming the tubular body comprises a plurality of constant sheet thickness sections separated by respective transition sections.

5. The device of claim 4, wherein the respective constant sheet thickness sections have differing cross-sectional thicknesses.

6. The device of claim 4, wherein the respective transition sections have a tapered cross-sectional thickness.

7. The device of claim 1, wherein portions of the flat sheet are removed to form openings therein.

8. The device of claim 1, wherein the elongate core defines a lumen therein.

9. An elongate medical device, comprising:
   an elongate core; and
   a substantially flat ribbon having portions removed to form openings, the ribbon spirally wound into a helical body defining a longitudinal axis and permanently secured to at least a portion of the elongate core,
   wherein the ribbon has a length, and wherein a cross-sectional thickness of the ribbon varies along the length of the ribbon.

10. The device of claim 9, wherein the helical body has a proximal portion and a distal portion, and wherein a cross-sectional thickness of the ribbon forming the distal portion of the helical body is thinner than a cross-sectional thickness of the ribbon forming the proximal portion of the helical body.

11. The device of claim 10, wherein a cross-sectional thickness of the ribbon forming the helical body tapers from the proximal portion to the distal portion.

12. The device of claim 9, wherein the ribbon forming the helical body comprises a plurality of constant ribbon thickness sections separated by respective transition sections.

13. The device of claim 12, wherein the respective constant ribbon thickness sections have differing thicknesses.

14. The device of claim 12, wherein the respective transition sections have a tapered cross-sectional thickness.

15. The device of claim 9, wherein the elongate core defines a lumen therein.

16. A method of forming an elongate medical device, comprising:
forming a substantially flat elongate sheet having a length into a tubular body by rolling the sheet about a longitudinal axis along the length of the sheet to form a tubular body having a length substantially the same length of the sheet, the sheet having a cross-sectional thickness, wherein the cross-sectional thickness varies along the length of the sheet; and
permanently securing the tubular body to an outer surface of an elongate core.

17. The method of claim 16, further comprising, prior to forming the sheet into a tubular body, removing portions from the sheet to define openings therein.

18. The method of claim 17, wherein removing portions from the sheet comprises etching or machining a pattern of openings in the sheet.

19. The method of claim 18, further comprising treating the rolled sheet using a technique selected from the group consisting of heat setting, tack welding, laser welding, mechanical attachment, chemical bonding, and adhering with an adhesive.

20. The method of claim 16, further comprising covering the tubular body with a polymer layer.

21. A method of forming an elongate medical device, comprising:
forming a substantially flat ribbon having portions removed to form openings into a helical body, the ribbon having a length and a cross-sectional thickness, wherein the cross-sectional thickness varies along the length of the ribbon; and
permanently securing the helical body to the outer surface of an elongate core.

22. The method of claim 21, wherein removing portions from the ribbon comprises etching or machining a pattern of openings in the ribbon.

23. The method of claim 21, further comprising covering the helical body with a polymer layer.

24. The method of claim 21, wherein the helical body has a longitudinal axis, and wherein forming the ribbon into a helical body comprises spirally winding the ribbon around the longitudinal axis.

25. The method of claim 24, further comprising treating the wound ribbon using a technique selected from the group consisting of heat setting, tack welding, laser welding, mechanical attachment, chemical bonding, and adhering with an adhesive.

* * * * *